United States Patent
Zhang

(10) Patent No.: US 12,042,717 B2
(45) Date of Patent: Jul. 23, 2024

(54) METHOD AND DEVICE FOR CONTROL OF A MOBILITY DEVICE USING AN ESTIMATED GAIT TRAJECTORY

(71) Applicant: Shift Robotics, Inc., Austin, TX (US)

(72) Inventor: Xunjie Zhang, Pittsburgh, PA (US)

(73) Assignee: Shift Robotics, Inc., Austin, TX (US)

( * ) Notice: Subject to any disclaimer, the term of this patent is extended or adjusted under 35 U.S.C. 154(b) by 365 days.

(21) Appl. No.: 17/421,479

(22) PCT Filed: Jan. 9, 2020

(86) PCT No.: PCT/US2020/012992
§ 371 (c)(1),
(2) Date: Jul. 8, 2021

(87) PCT Pub. No.: WO2020/146680
PCT Pub. Date: Jul. 16, 2020

(65) Prior Publication Data
US 2022/0062743 A1    Mar. 3, 2022

Related U.S. Application Data

(60) Provisional application No. 62/790,412, filed on Jan. 9, 2019.

(51) Int. Cl.
*A61B 5/11* (2006.01)
*A63C 17/12* (2006.01)

(52) U.S. Cl.
CPC ............ *A63C 17/12* (2013.01); *A61B 5/112* (2013.01); *A63C 2203/18* (2013.01); *A63C 2203/22* (2013.01)

(58) Field of Classification Search
CPC ................................ A63C 17/12; A61B 5/112
See application file for complete search history.

(56) References Cited

U.S. PATENT DOCUMENTS

| | | |
|---|---|---|
| 1,672,700 A | 6/1928 | Vass |
| 1,801,205 A | 4/1931 | Mirick |
| 3,392,986 A | 7/1968 | Ryan et al. |
| 4,417,737 A | 11/1983 | Suroff |
| 4,932,676 A | 6/1990 | Klamer |
| 5,236,058 A | 8/1993 | Yamet et al. |
| 5,413,380 A | 5/1995 | Fernandez |
| 5,730,241 A | 3/1998 | Shyr et al. |

(Continued)

FOREIGN PATENT DOCUMENTS

| | | |
|---|---|---|
| CN | 201423154 Y | 3/2010 |
| CN | 201565096 U | 9/2010 |

(Continued)

OTHER PUBLICATIONS

European Supplementary Search Report for EP18831335.7 dated Feb. 3, 2021.

(Continued)

*Primary Examiner* — Erez Gurari
(74) *Attorney, Agent, or Firm* — DLA PIPER LLP (US)

(57) ABSTRACT

A system for control of a mobility device comprising a controller for analyzing data from at least one sensor on the mobility device, wherein the data is used to determine the gait trajectory of a user. The gait data is then used to provide motion command to an electric motor on the mobility device.

18 Claims, 5 Drawing Sheets

(56) References Cited

U.S. PATENT DOCUMENTS

| | | |
|---|---|---|
| 5,797,466 A | 8/1998 | Gendle |
| 6,059,062 A | 5/2000 | Staelin et al. |
| 6,322,088 B1 | 11/2001 | Klamer et al. |
| 6,425,587 B1 | 7/2002 | Moon |
| 6,497,421 B1 | 12/2002 | Edgerley et al. |
| 6,645,126 B1 | 11/2003 | Martin et al. |
| 7,163,210 B1 | 1/2007 | Rehkemper et al. |
| 7,204,330 B1 | 4/2007 | Lauren |
| 9,027,690 B2 | 5/2015 | Chavand |
| 9,295,302 B1 | 3/2016 | Reed et al. |
| 9,925,453 B1 | 3/2018 | Tuli |
| 10,456,698 B2 | 10/2019 | Chen et al. |
| 10,709,961 B2 | 7/2020 | Zhang et al. |
| 10,933,298 B2 | 3/2021 | Zhang et al. |
| 10,933,299 B2 | 3/2021 | Zhang et al. |
| 2001/0022433 A1 | 9/2001 | Chang |
| 2003/0047893 A1 | 3/2003 | Pahis |
| 2003/0141124 A1 | 7/2003 | Mullet |
| 2005/0046139 A1 | 3/2005 | Guan |
| 2005/0082099 A1 | 4/2005 | Tuli |
| 2006/0027409 A1 | 2/2006 | Adams et al. |
| 2007/0273110 A1 | 11/2007 | Brunner |
| 2008/0093144 A1 | 4/2008 | Manor |
| 2009/0120705 A1 | 5/2009 | McKinzie |
| 2010/0207348 A1 | 8/2010 | Othman |
| 2012/0285756 A1 | 11/2012 | Treadway |
| 2013/0025955 A1 | 1/2013 | Chavand |
| 2013/0123665 A1 | 5/2013 | Mariani et al. |
| 2013/0226048 A1 | 8/2013 | Unluhisarcikli et al. |
| 2013/0274640 A1 | 10/2013 | Butters et al. |
| 2013/0282216 A1* | 10/2013 | Edney .................. A63C 17/04 701/22 |
| 2014/0196757 A1 | 7/2014 | Goffer |
| 2015/0196403 A1 | 7/2015 | Kim et al. |
| 2015/0196831 A1 | 7/2015 | Treadway et al. |
| 2015/0352430 A1 | 12/2015 | Treadway et al. |
| 2016/0045385 A1 | 2/2016 | Aguirre-Ollinger et al. |
| 2016/0058326 A1 | 3/2016 | Winfree et al. |
| 2016/0113831 A1 | 4/2016 | Hollander |
| 2016/0250094 A1 | 9/2016 | Amundson et al. |
| 2016/0331557 A1 | 11/2016 | Tong et al. |
| 2017/0055880 A1 | 3/2017 | Agrawal et al. |
| 2017/0181917 A1 | 6/2017 | Ohta et al. |
| 2017/0182397 A1 | 6/2017 | Zhang |
| 2017/0259162 A1 | 9/2017 | Mo |
| 2017/0259811 A1 | 9/2017 | Coulter et al. |
| 2017/0296116 A1 | 10/2017 | McCarthy et al. |
| 2018/0008881 A1 | 1/2018 | Mo |
| 2018/0015355 A1 | 1/2018 | Desberg et al. |
| 2018/0333080 A1 | 11/2018 | Malawey et al. |
| 2019/0061557 A1* | 2/2019 | Quick .................. A63C 17/12 |
| 2019/0184265 A1 | 6/2019 | Micacchi |
| 2019/0314710 A1 | 10/2019 | Zhang et al. |
| 2019/0351315 A1* | 11/2019 | Li ......................... B62K 13/00 |
| 2020/0000373 A1* | 1/2020 | Agrawal ............. A61B 5/7267 |
| 2020/0061444 A1 | 2/2020 | Zhang et al. |
| 2020/0061445 A1 | 2/2020 | Zhang et al. |
| 2020/0129843 A1 | 4/2020 | Zhang et al. |
| 2020/0129844 A1 | 4/2020 | Zhang et al. |
| 2020/0197786 A1 | 6/2020 | Artemev |
| 2021/0015200 A1 | 1/2021 | Tuli |
| 2021/0113914 A1* | 4/2021 | Zhang .................. B60L 7/26 |

FOREIGN PATENT DOCUMENTS

| | | |
|---|---|---|
| CN | 101912680 A | 12/2010 |
| CN | 101912681 A | 12/2010 |
| CN | 102278988 A | 12/2011 |
| CN | 102805928 A | 12/2012 |
| CN | 203389316 U | 1/2014 |
| CN | 104689559 A | 6/2015 |
| CN | 204364838 U | 6/2015 |
| CN | 204395401 U | 6/2015 |
| CN | 105214299 A | 1/2016 |
| CN | 106039689 A | 10/2016 |
| CN | 205627021 U | 10/2016 |
| CN | 106390428 A | 2/2017 |
| CN | 106390430 A | 2/2017 |
| CN | 106582003 A | 4/2017 |
| CN | 108186024 A | 6/2018 |
| CN | 108836346 A | 11/2018 |
| EP | 0686412 A2 | 12/1995 |
| EP | 0834337 A2 | 4/1998 |
| EP | 0894515 A1 | 2/1999 |
| EP | 3629925 A1 | 4/2020 |
| GB | 2452563 A | 3/2009 |
| IN | 102167117 A | 8/2011 |
| JP | 2005-81038 A | 3/2005 |
| JP | 2013111118 A | 6/2013 |
| WO | 2011092443 A2 | 8/2011 |
| WO | 2018082192 A1 | 5/2018 |
| WO | 2018082193 A1 | 5/2018 |
| WO | 2018082194 A1 | 5/2018 |
| WO | 2018082195 A1 | 5/2018 |
| WO | 2019014152 A1 | 1/2019 |
| WO | 2019014154 A1 | 1/2019 |
| WO | 2019212995 A1 | 11/2019 |
| WO | 2020146680 A1 | 7/2020 |

OTHER PUBLICATIONS

International Search Report and Written Opinion for PCT/CN2017/000499 dated Oct. 20, 2017.
International Search Report and Written Opinion for PCT/CN2017/000500 dated Oct. 20, 2017.
International Search Report and Written Opinion for PCT/CN2017/000501 dated Nov. 3, 2017.
International Search Report and Written Opinion for PCT/CN2017/000502 dated Oct. 13, 2017.
International Search Report and Written Opinion for PCT/US2018/041343 dated Sep. 7, 2018.
International Search Report and Written Opinion for PCT/US2018/041345 dated Sep. 7, 2018.
International Search Report and Written Opinion for PCT/US2019/029742 dated Aug. 26, 2019.
International Search Report and Written Opinion for PCT/US2020/012992 dated Apr. 1, 2020.
International Search Report and Written Opinion for PCT/US2021/056014 dated Jan. 18, 2022.

* cited by examiner

METHOD AND DEVICE FOR CONTROL OF A MOBILITY DEVICE USING AN ESTIMATED GAIT TRAJECTORY

CROSS-REFERENCE TO RELATED APPLICATIONS

This application is a U.S. national stage filing under U.S.C. § 371 of International PCT Application No. PCT/US2020/012992 filed Jan. 9, 2020, and titled "A Method and Device for Control of a Mobility Device Using an Estimated Gait Trajectory," which in turn claims the benefit under 35 U.S.C. § 119 of U.S. Provisional Application No. 62/790,412, filed Jan. 9, 2019, which is incorporated by reference herein.

STATEMENT REGARDING FEDERALLY SPONSORED RESEARCH

Not applicable.

BACKGROUND OF THE INVENTION

The invention relates to a mobility device. More specifically, the invention relates to a control system and method of controlling a mobility device that is worn on the feet of a user to provide mobility assistance.

Commuters and other travelers often have to walk the final leg of their trip, regardless of whether they travelled by car, bus, train, or other means. Depending on the distance, the time needed to complete this final leg of the journey can comprise a significant amount of the total duration of the trip. While prior systems have utilized a control system in connection with wheeled, foot-worn mobility devices, these systems implemented motor controls that lacked precision or coordination with the user's actual movements. Fundamentally, those control systems require the user to perform an unnatural and unintuitive movement to control the speed. For example, motorized roller-skate like devices require human users to either lean their body back and forth or operate a hand-held controller to accelerate or decelerate. On the other hand, a human, as a bipedal walking subject, is used to adjusting her speed, turning, and climbing hills by adjusting her gait, i.e. stride length and cadence. Therefore, it would be advantageous to develop a control system for a mobility device that provides improved control to augment gait performance.

BRIEF SUMMARY

According to embodiments of the present invention is system and method of controlling a mobility device or a pair of mobility devices, wherein one mobility device of the pair is worn on each foot of a user. A sensor or a group of sensors in each mobility device obtains data about the motion of the user, or the mobility device attached to a foot of the user, and transmits the data to a processor, which may be housed in one or both devices of the pair. The processor analyzes the motion data to develop commands for each mobility device. Each mobility device may comprise a motor, gearing, and wheels and is adapted to be worn on the foot of a user. In one embodiment, the mobility devices are worn over the user's shoes. When worn on the feet of a user, the mobility devices allow a user to walk at an increased rate of speed for a given cadence and stride length, as compared to their speed without the mobility devices. Further, the control system adapts to a user so no learning or other control inputs are required by the user.

DETAILED DESCRIPTION

Figure 1:
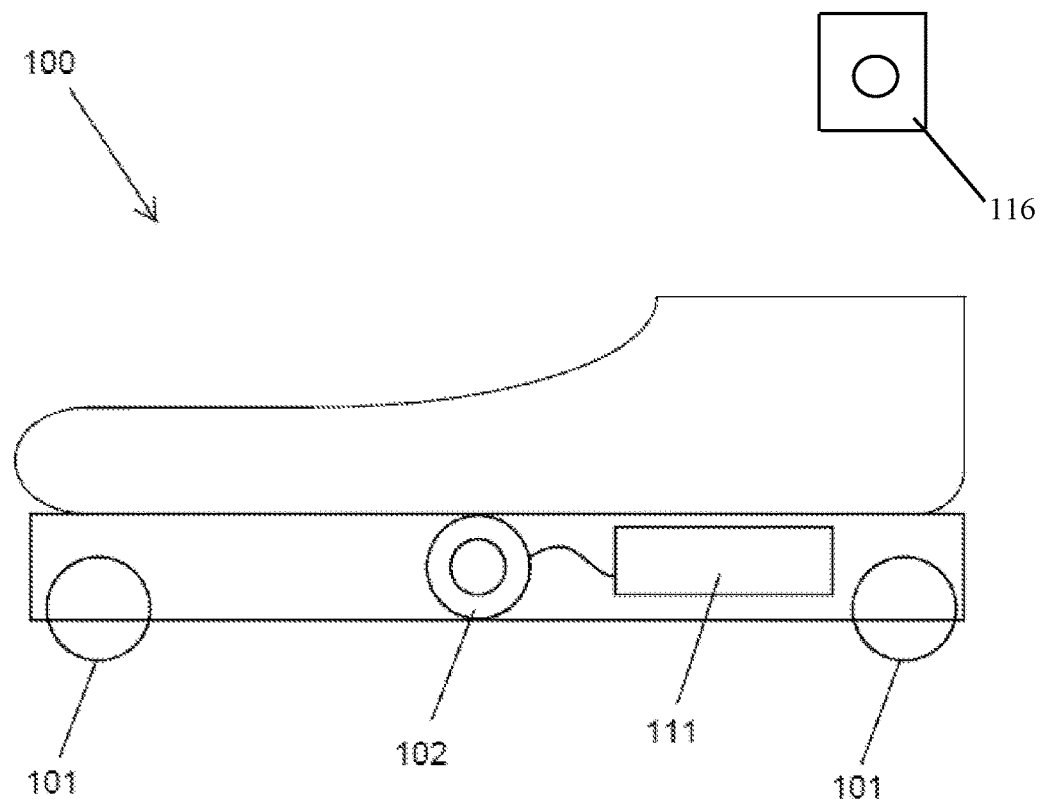
FIG. 1 depicts a mobility device with an embedded controller and an optional remote master switch.

As shown in FIG. 1, a mobility device 100, according to one embodiment, comprises a plurality of wheels 101, with at least one of the wheels 101 connected to an electric motor 102. The wheels 101 can be connected to the motor 102 through gearing or a belt, alternatively, directly connected to the motor 102. In one embodiment, the mobility device 100 may further comprise a rear chassis and a front chassis, connected by a flexible joint, to enable normal flexion of the user's foot while walking. During typical use, a user will wear two mobility devices 100, one on each foot. The mobility device 100 enables a pedestrian to walk faster than a normal walking pace by adding torque to at least one of the wheels 101 when that wheel 101 is in contact with the ground. In this manner, the user experiences an effect similar to that of walking on a moving walkway.

Further shown in FIG. 1 is an onboard controller 111, which enables a user to maintain a normal walking motion by adapting the control of the motor 102 to the movements of the user. As will be discussed in greater detail, the speed at which the wheels 101 spin, through a torque applied by the motor 102, is controlled in part by an analysis of the user's motion or gait. In some embodiments, the motion of the pair of devices 100 worn by the user are analyzed together to provide better control than single-foot control methods.

In one embodiment, the components of the onboard controller 111 may comprise at least one inertial measurement unit or other sensors 113, a processor, a motor driver, and a wireless communication module. In this disclosure, the controller 111 and components of the controller 111, including drivers and modules, may comprise a microcomputer, a microprocessor, a microcontroller, an application specific integrated circuit, a programmable logic array, a logic device, an arithmetic logic unit, a digital signal processor, or another data processor and supporting electronic hardware and software. Further, the components of the controller 111 may be standalone units or may be integrated as part of the controller 111. In one embodiment, the system comprises two onboard controllers 111, or one for each mobility device (i.e. one for each foot of the user). However, in alternative embodiments, a single controller 111 may be used. In the embodiment where a single controller 111 is used, data from an inertial measurement unit 113 in each device 100 of a pair may be sent wirelessly to the single controller 111.

The controller 111 is used to collect data and analyze the gait or walking motion of a user and to generate a motion command. For example, the onboard processor reads motion data, which may comprise acceleration, angular rates, orientation, gyroscopic data, or quaternion data of the mobility device 100 from the inertial measurement unit 113. Based on this data, the controller 111 will generate a motion command according to the control method discussed herein. The motion command comprises, for example, acceleration to a set speed, braking, deceleration to a set speed, and holding at a constant speed. Upon receiving the motion command, the onboard processer along with the motor driver converts the motion command into a motor driving signal and drives the motor system 102, thereby affecting the speed of the wheels 101. In one embodiment, the motor driver receives a speed command and drives the motor 102 at the command speed via a feedback loop control.

Figure 2:
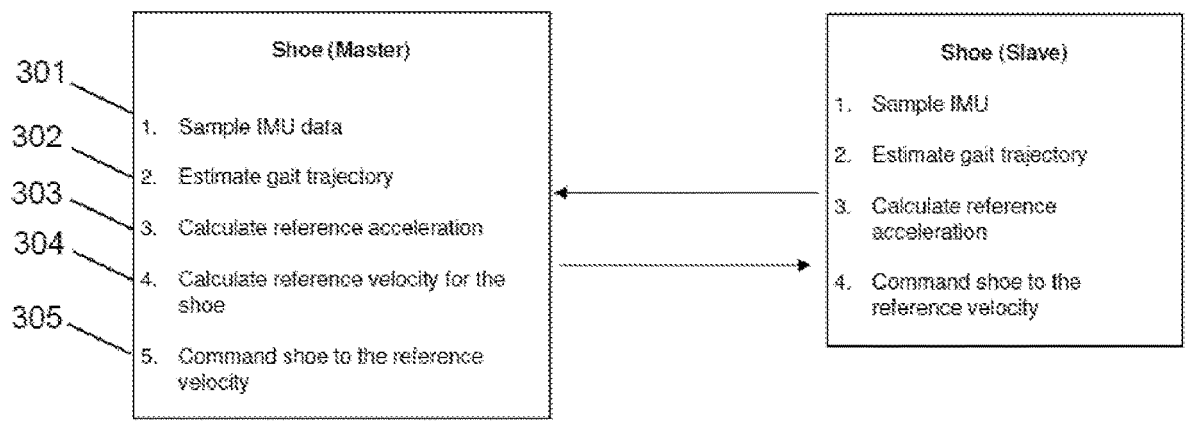
FIG. 2 depicts the processes performed in each mobility device of a pair, according to one embodiment.

The diagram shown in FIG. 2 depicts the method of motion control, according to one embodiment where the mobility devices 100 are operating in slave/master configuration, comprising: receiving motion dynamic data from the sensors 113 at step 301, estimating the gait trajectory at step 302, calculating the reference acceleration at step 303, calculating the reference velocity at step 304, and commanding the mobility device 100 to the reference velocity at step 305. The preceding steps apply to a first mobility device 100 of the pair of mobility devices 100, or the master mobility device. The second mobility device is known as the slave mobility device, and uses a similar method, but receives the command velocity from the master mobility device. By using a master/slave configuration, disparities between the two mobility devices 100 can be avoided. However, in alternative embodiments, each mobility device 100 of the pair operates as a 'master' or can be controlled independently.

By way of further detail, in step 301, the controller 111 samples motion data from the inertial measurement unit or other sensors 113. Data may include acceleration and gyroscopic rate and orientation data, and torque indication from motor current. Next, in step 302, the controller 111 estimates the gait trajectory, which can include swing velocities and distances in three dimensions. During this step, a stance detection process is used to determine whether an individual device 100 is in the stance or swinging phase of the gait cycle. Two methods can be used to detect the stance.

For the first stance detection method, the results of three sub-steps are analyzed over a period of time to determine the gait phase. In the first sub-step, generalized likelihood ratio tests are run over an array of linearized acceleration and gyro sets for likelihood of gait phase. Next, in the second sub-step, angular velocity data in multiple dimensions is compared to a predefined threshold. If all angular velocities are below a threshold, then the device 100 is likely to be in the stance phase. In the third sub-step, the motor current is compared with a threshold. Higher than threshold current implies the possibility of the stance phase. Conversely, a motor current below the threshold indicates a swing phase, as there is no force from the pavement being applied to the wheel. If all three sub-steps indicate the device 100 is in the stance phase for a period of time (for example, about 50-100 ms), then the mobility device 100 is determined as being in the stance phase. If not, then the mobility device 100 is in the swing phase. By using a statistical analysis, the stance determination is less affected by noise and outliers in the data received from the inertial measurement unit 113, creating a more robust control method.

For the second stance detection method, either roll or yaw angular velocities are compared to thresholds and the pitch angular velocity is checked to determine if it falls within a pre-determined range. If either roll or yaw angular velocities is above the thresholds, then the device 100 is likely in the swing phase. If both roll and yaw angular velocities are below the thresholds, and the pitch angular velocity is within the pre-determined range for a short period of time (for example, 50-100 ms), then the device 100 is likely in the stance phase, otherwise the device 100 is in the swing phase. The threshold values and pre-determined ranges are generic for all types of gaits and are average measurements from a large data set of collected user gait data. However, a person having skill in the art will appreciate that methods, other than taking an average, can be used to define the threshold and range values. Further, if a device 100 is moving, the motor current is compared with a threshold. Higher than threshold current, in addition to the previous analysis of roll, yaw, and pitch, indicates stance phase when the conditions are met for a period of time (50-100 ms, for example).

In various steps of the method, analysis of data is performed in either a global frame or a body frame. Global frame is defined with respect to the inertial frame which does not change, whereas body frame is defined with respect to the body of the shoe or mobility device 100. To further estimate the gait trajectory in step 302, acceleration under the body frame is converted to the global frame based on a corrected orientation, which is the current orientation less an offset which was recursively calculated in a previous iteration of the gait trajectory estimation. Acceleration data is then filtered in the global frame to remove noises. Velocity can then be determined as a single integration of the acceleration data. A Kalman filter is then used to obtain corrected velocities by offsetting acceleration integrated velocity with an error term generated by the Kalman filter. Next, the velocities are integrated and corrected in the same way as obtaining corrected velocities to obtain corrected swing distance in the global frame. The velocities and swing distance data are then converted into the local frame by applying orientation measured at the point at which the mobility device 100 transitions from the stance to swing phase. By applying error terms to both accelerations and velocities integrations, swing distance can be estimated in real time with minimal drift. This is an improvement over previous systems, which computes swing distance at the end of a swing phase, when the de-drift term is calculated. By analyzing a full step, prior control methods suffered from lag as the speed was assumed to be the same as a previous step until the new distance is updated.

As noted, the Kalman filter is used to estimate error terms for velocities and swing distances by calculating an estimation error recursively based on an assumption of zero velocity when the mobility device 100 is in the stance (i.e. foot on-ground) phase. When the swing phase is detected, the Kalman filter stops calculating and all its terms remains unchanged. Its error term is applied to velocity.

Figure 3:
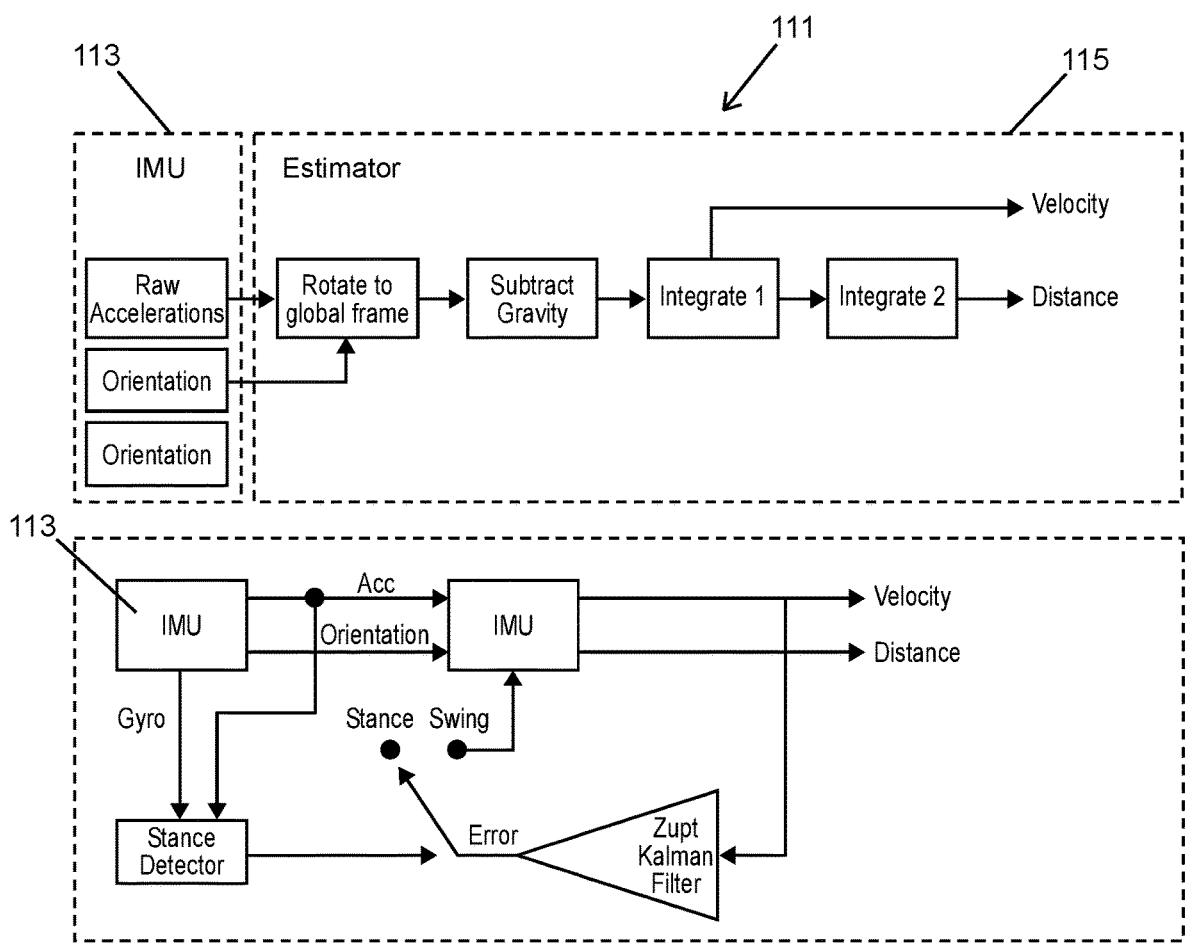
FIG. 3 is a block diagram of a control system, according to one embodiment.

FIG. 3 shows a block diagram of a controller 111 incorporating an inertial measurement unit 113 and an estimator module 115. As previously discussed, the estimator and other components of the controller 111 may comprise software, firmware, hardware, or any combination of hardware/software.

At step 303, the reference acceleration is calculated based on the swing velocity and distance identified in the previous step. During this step, the swing velocity is normalized by subtracting a drag constant and then multiplied with a proportional gain, which is a coefficient obtained through tuning, to obtain the velocity-based reference acceleration. The drag constant can be adjusted in real time as a function of the actual velocity of the device 100.

Figure 4:
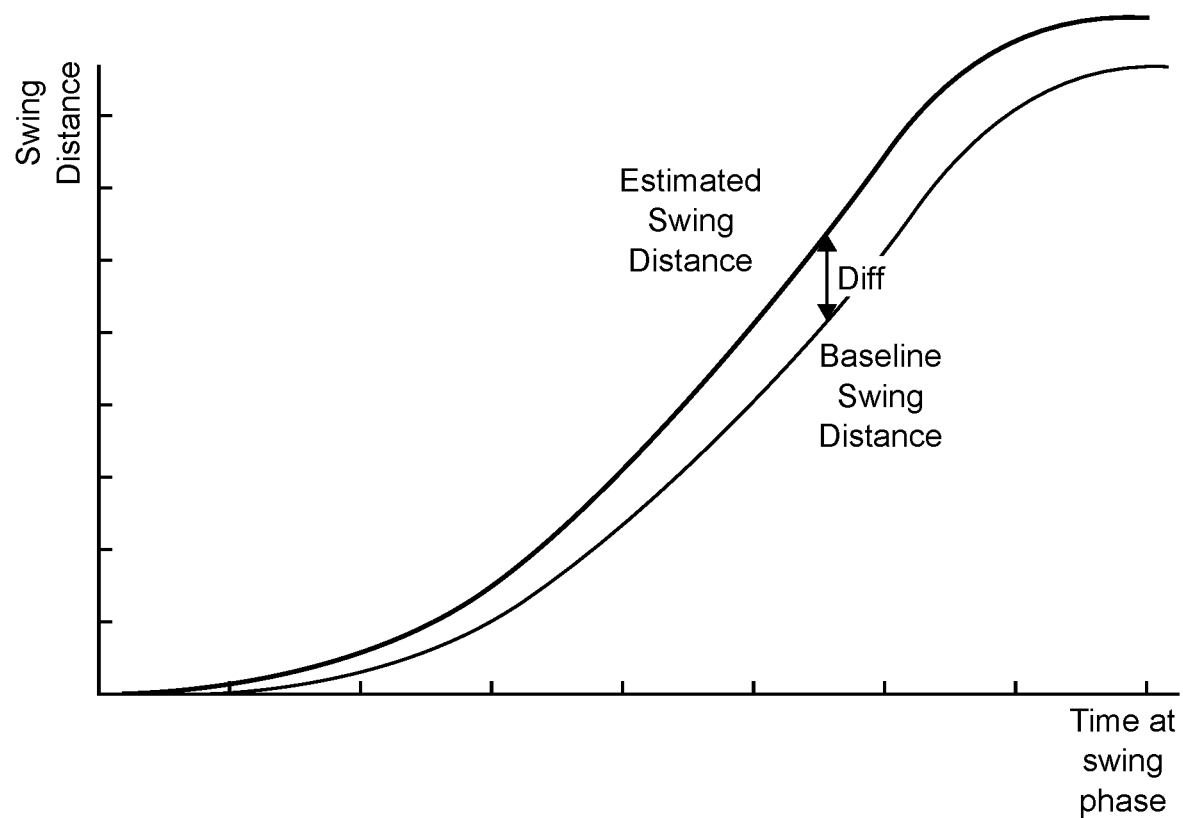
FIG. 4 is a graph showing an estimated swing distance as compared to a baseline swing distance.

To obtain swing distance-based reference acceleration, the difference between the estimated and baseline swing distance is extrapolated at the elapsed time during the swing phase. The difference between the estimated swing distance and the baseline swing distance is shown on the graph in FIG. 4. The swing-distance based reference acceleration is a product of the swing distance difference and the proportional gain. The total reference acceleration is a product of both swing distance-based acceleration and velocity-based reference acceleration.

Figure 6:
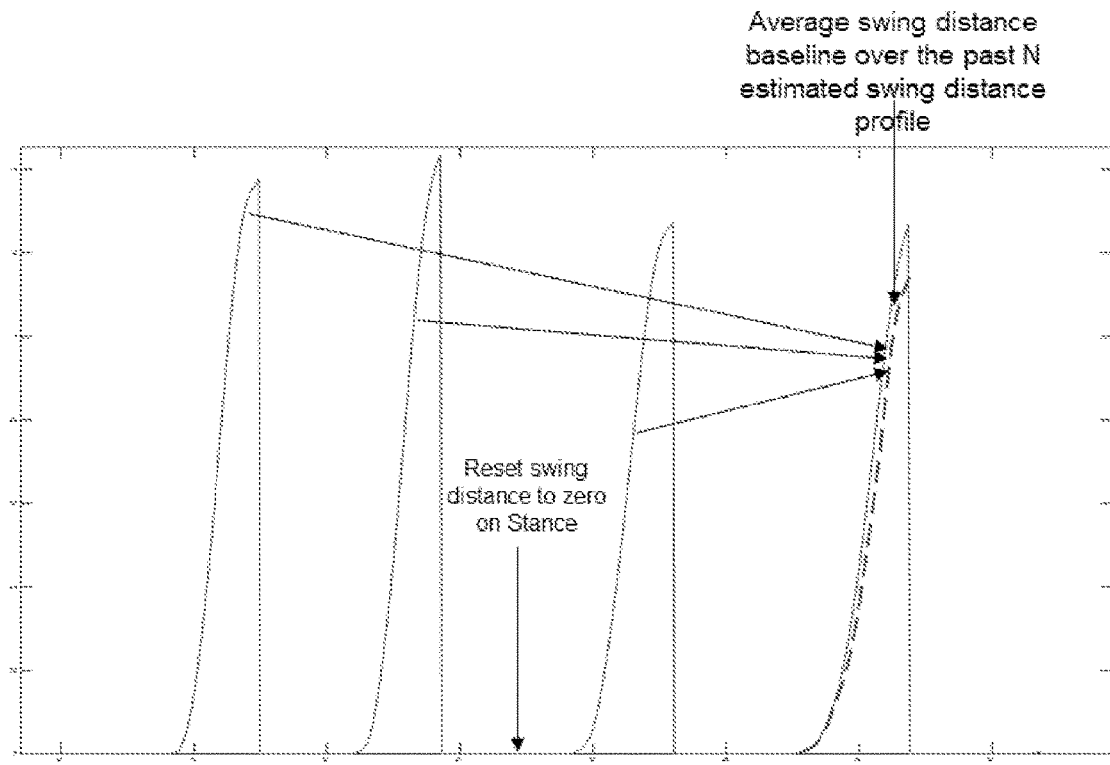
FIG. 6 is a graph showing baseline swing distance is calculated as a weighted average of past estimated swing distances.

The baseline swing distance can be pre-determined (for example, an average over a large data set) or, alternatively, approximated from the weighted average of most recent estimated swing distances. For example, the baseline swing distance can be based on a weighted average of the past N number of estimated swing distance profiles, shown on the graph in FIG. 6, where N is an adjustable constant. The baseline swing distance can also be described by an approximation function such as polynomial fit, linear regression or spline interpolation.

Figure 5:
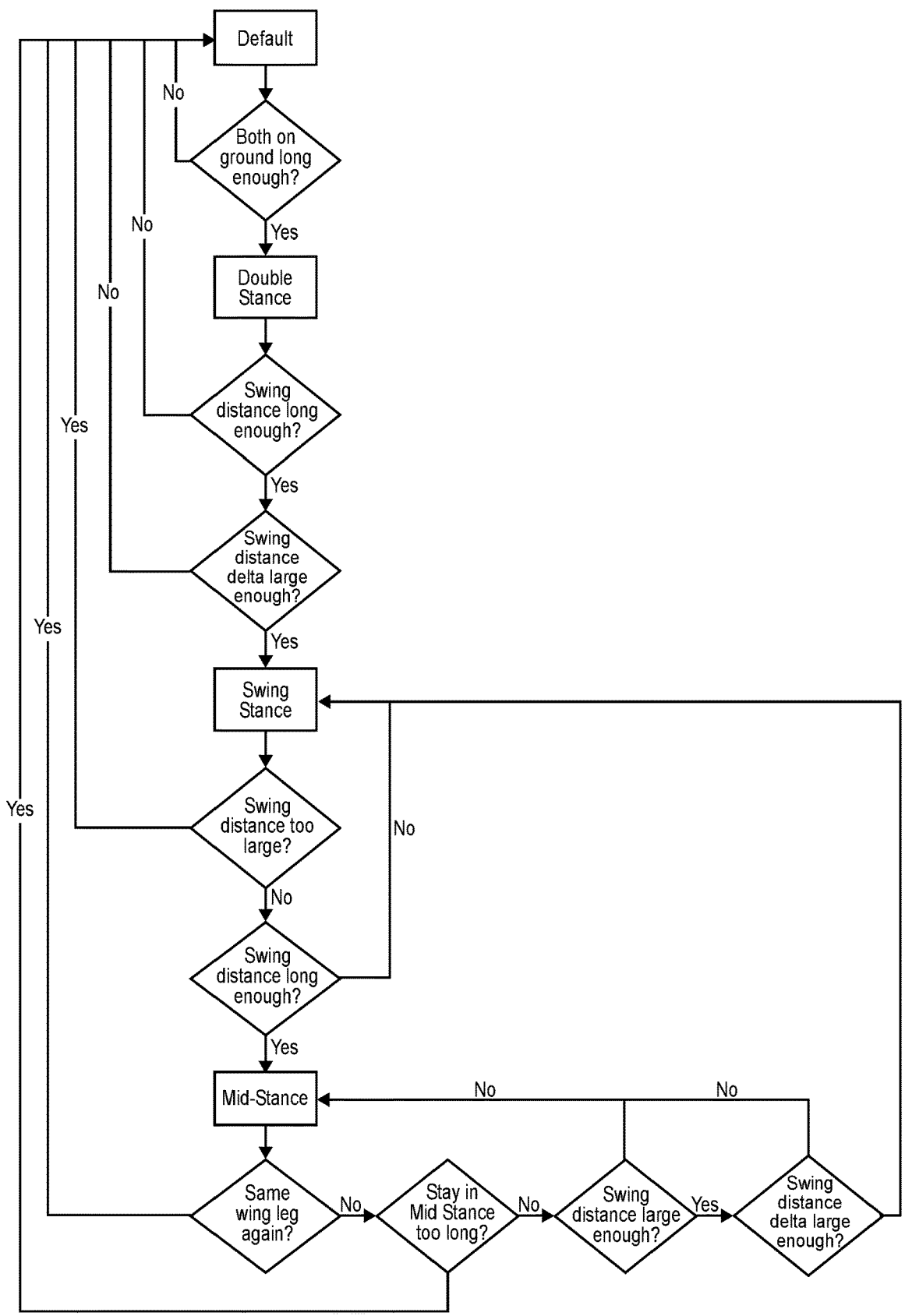
FIG. 5 is a flow diagram related to a gait cycle state machine.

At step 304, the reference velocity for the mobility device 100 is calculated based on the total reference acceleration through discrete integration. A reference velocity for both mobility devices 100 is calculated from the reference acceleration of the swing leg only since the reference acceleration of the stance leg is zero. A gait state machine is used to classify the user gait into three different stages, in addition to a default phase: Double Stance, Swing Stance, and Mid-Stance phase as shown in flow diagram depicted in FIG. 5. The gait state machine, which can be implemented in the controller 111, looks at the pair of devices 100 together to determine an overall gait phase of the user. In contrast, the stance detection method, as noted previously, is directed to a single device 100. As shown in FIG. 5, the controller 111, through the gait state machine, determines if: (1) both feet are on the ground (i.e. Double Stance); (2) if and only if one leg's swing distance is sufficiently large and if the swing distance difference between two legs is sufficiently large (i.e. Swing Stance); and (3) if one leg just enters the stance phase and the other leg has not entered the swing phase (i.e. Mid-Stance).

The gait state machine always starts with Default phase and only enters Double Stance after detecting both feet in Stance phase for a few seconds. In both the Default and Double Stance phases, the reference acceleration and reference velocity are set as zero.

During the Double Stance phase, if and only if one device's 100 swing distance is sufficiently large and if the swing distance difference between two legs is sufficiently large, the gait state machine enters into Swing Stance phase. The total reference acceleration is only integrated to the reference velocity during the Swing Stance phase. If the swing distance exceeds the minimal stride length in continuous walking, a forward step flag is raised. When the forward step is active and if the swing distance is larger than a max stride length, a fault flag will be raised and the state machine will return to the Default phase, meaning the reference acceleration and reference velocity are set to zero. As such, the fault flag acts as a safety feature in certain circumstances. When the forward step is active and if the swing distance decreases below the minimal stride length, the state machine enters Mid-Stance phase as the step is completed.

During Mid-Stance phase, if and only if the other foot's swing distance is sufficiently large and if the swing distance difference between two legs is sufficiently large, the state machine returns to Swing Stance phase. The Stance-Swing and Mid-Stance phases will continue alternating as the cyclic motion of bipedal walking.

However, if the same foot clearly swings again, the state machine resets to Default phase as a result of an unusual event and a fault flag will be raised. If both legs stay in Stance for too long (for example, ~1 s) or both of their stride lengths indicate forward step during Mid-Stance phase, the state machine resets to Default phase and raises an fault flag. During Mid-Stance phase, the reference velocity decelerates based on the elapsed time and actual mobility device velocity. The deceleration profile prevents abrupt stop upon the user completes a step while ensures the control system promptly responds to user stop motion (planting both feet on ground firmly).

Figure 7:
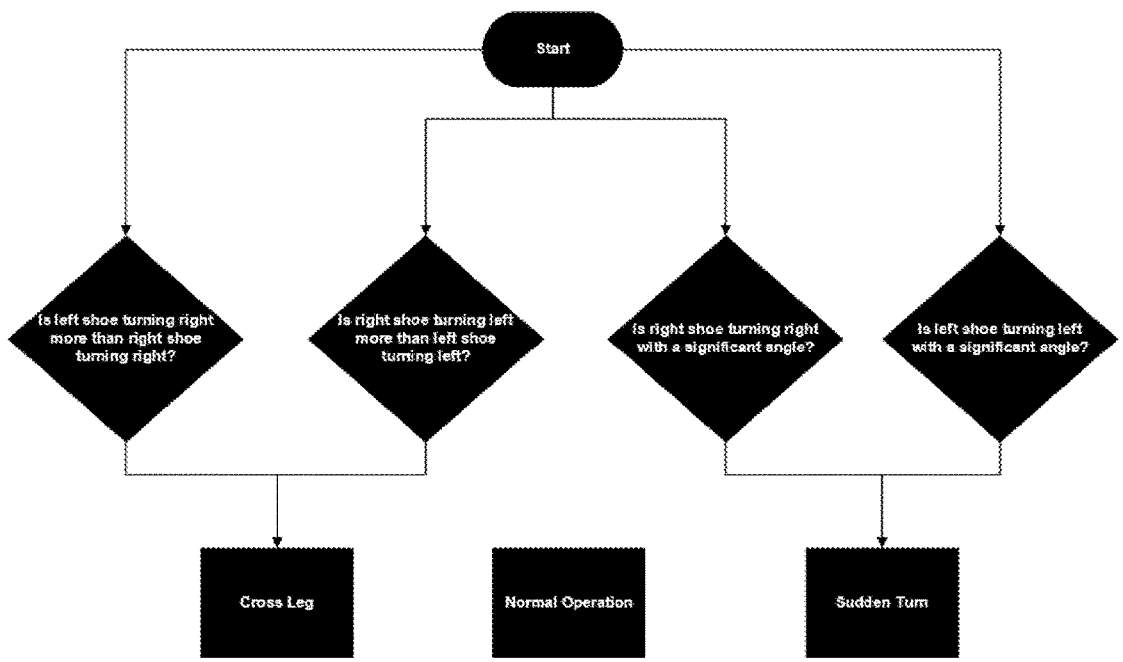
FIG. 7 is a flow diagram showing detection of cross-leg and sudden turn events.

In addition to detecting various gait phases, the controller 111 can detect other abnormal gait patterns. For example, if a cross-leg motion or sudden turn is detected as shown in FIG. 7, the control system immediately reduces reference velocity based on the cross-leg or turning angles. Similarly, when the user applies an emergency brake, the motor increases its current to respond to the increased drag force. If a sudden motor current increased is detected during Double Stance phase, the control system immediately reduces the reference velocity based on the magnitude of the current.

Ascending or descending stairs presents another challenge that the controller 111 will detect and control without any input from the user. For example, the height difference is calculated between the beginning and the end of the swing leg at all times. If the magnitude of the height difference is similar or larger than an average stair step height, the stair mode is activated and both mobility devices 100 are locked to prevent wheel 102 rotation. This feature allows user to climb up and down stairs without removing the mobility devices 100 from his feet to ascend or descend the stairs. Once the stair mode is activated, it will remain locked for a short period of time, such as 2-3 seconds for example.

As previously discussed, the gait state machine explores a more holistic relationship of both legs' motion in bipedal walking, in contrast to interpedently controlled self-balancing skates. It allows for a smooth transition between walking and skating motion (i.e. gliding between steps) at any time while still being responsive to the change of user gait. For example, the user can rapidly speed up the mobility devices by making largest and fastest strides and once a satisfactory speed level is reached, the user can cruise at that speed even at slightly smaller and slower strides. In the event of stopping, the user controls the aggressiveness of braking by from proportionally reducing the stride length/cadence to planting both feet on ground.

The reference velocity is shared between each mobility device 100 in the pair. The reference velocity is set to zero when both mobility device 100 are in stance phase for a pre-defined period of time. At step 305, the motor controller will drive each mobility device 100 towards the reference velocity with a feedback control loop.

In one embodiment, a remote master switch 116 (as shown in FIG. 1) is provided and will communicate wirelessly with either the master device or both devices simultaneously. The remote master switch 116 can either switch on the control system operating as described above or override any control system output with a brake command, which holds the mobility device 100 at zero velocity. This external switch helps the user to travel through certain terrains without taking off mobility devices, for example walking across significantly cracked and bumpy sidewalks where wheel 102 rotation is undesirable.

In any part of speed ramping up and down, there are absolute max acceleration and deceleration limiters to ensure safe and healthy operations for both users and mobility devices.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilized for realizing the invention in diverse forms thereof. In particular, one or more features in any of the embodiments described herein may be combined with one or more features from any other embodiments described herein.

Protection may also be sought for any features disclosed in any one or more published documents referred to and/or incorporated by reference in combination with the present disclosure.

What is claimed is:

1. A method of controlling a pair of mobility devices comprising:
    receiving data from at least a first sensor in a first mobility device or a second sensor in a second mobility device;
    estimating a gait trajectory;
    calculating a reference acceleration;
    calculating a reference velocity based on the reference acceleration and a gait phase determined by a gait state machine, wherein the gait state machine classifies a user gait into three phases consisting of a double stance phase, a swing stance phase, and a mid-stance phase; and
    commanding a motor and at least one wheel connected to the motor in each of the first mobility device and the second mobility device to the reference velocity.

2. The method of claim 1, wherein at least one of the first sensor and the second sensor is an inertial measurement unit.

3. The method of claim 1, wherein estimating a gait trajectory comprises:
    identifying the gait phase as either a stance phase or a swing phase;
    determining a swing velocity through integration of acceleration,
    obtaining a corrected swing velocity, using a Kalman filter, by offsetting the swing velocity with an error term; and
    determining a swing distance through integration of the corrected swing velocity,
    wherein determining the swing velocity and determining the swing distance occur only during the swing phase.

4. The method of claim 3, wherein identifying the gait phase comprises:
    running a generalized likelihood ratio test on an array of linearized acceleration and gyro sets for a likelihood of gait phase;
    comparing angular velocity in at least one dimension to an angular velocity threshold; and
    comparing a current of the motor to a current threshold.

5. The method of claim 3, wherein identifying the stance phase comprises:
    comparing at least one of roll angular velocity and yaw angular velocity to a velocity threshold;
    identifying whether pitch angular velocity is within a pre-determined range; and
    comparing a current of the motor to a current threshold.

6. The method of claim 1, wherein calculating a reference acceleration comprises:
    normalizing a swing velocity identified in the gait trajectory by subtracting a drag constant and multiplying with a proportional gain;
    determining a swing distance difference as a difference between an estimated swing distance and a baseline swing distance; and
    calculating the reference acceleration as a product of the swing distance difference and the normalized swing velocity.

7. The method of claim 6, wherein the baseline swing distance is a pre-determined value.

8. The method of claim 6, wherein the baseline swing distance is estimated from a weighted average of previous estimated swing distances.

9. The method of claim 1, wherein calculating a reference velocity comprises:
    deriving the reference velocity from the reference acceleration, wherein the reference velocity is set to zero if the gait phase identified by the gait state machine is default or double stance.

10. The method of claim 1, wherein the double stance phase is identified when each mobility device is in a stance phase for a period of time.

11. The method of claim 3, wherein the swing stance phase is identified if and only if the swing distance is sufficiently large and if a swing distance difference between the first mobility device and the second mobility device is sufficiently large.

12. The method of claim 1, wherein the mid-stance phase is identified if the first mobility device enters a stance phase and the second mobility device has not yet entered a swing phase.

13. The method of claim 1, further comprising:
    identifying a cross-leg motion from the data and reducing the reference velocity.

14. The method of claim 1, further comprising:
    identifying a stopping motion from the data and rapidly increasing an electrical current to the motor to reduce rotation of the at least one wheel.

15. The method of claim 1, further comprising:
    reducing the reference velocity when the gait state machine identifies the double stance phase and a sudden change in electrical current is detected from the motor, wherein the reference velocity is reduced proportionally to a magnitude of the sudden change in electrical current.

16. The method of claim 1, further comprising:
    preventing rotation of the at least one wheel when a magnitude of a height difference between a beginning and an end of a stride is equal to or greater than an average stair step height.

17. The method of claim 1, further comprising:
    overriding the controller using a remote.

18. The method of claim 1, further comprising:
    identifying a sudden turn when the data indicates that each of the first mobility device and the second mobility device are turning above a threshold angle; and reducing the command velocity in proportion to a difference between the angle and a baseline angle.

\* \* \* \* \*